(12) United States Patent
Fontaine et al.

(10) Patent No.: US 10,513,503 B2
(45) Date of Patent: Dec. 24, 2019

(54) USE OF 3-DEOXYANTHOCYANIDINS FOR TREATING OCCULAR DISEASES

(71) Applicants: BIOPHYTIS, Paris (FR); UNIVERSITE PIERRE ET MARIE CURIE—PARIS 6 (UPMC), Paris (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

(72) Inventors: Valerie Fontaine, Cachan (FR); Rene Lafont, Paris (FR); Jose-Alain Sahel, Paris (FR); Stanislas Veillet, Savigny-sur-Orge (FR)

(73) Assignees: BIOPHYTIS, Paris (FR); SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE, Paris (FR)

(*) Notice: Subject to any disclaimer, the term of this patent is extended or adjusted under 35 U.S.C. 154(b) by 0 days.

(21) Appl. No.: 15/577,173

(22) PCT Filed: May 27, 2016

(86) PCT No.: PCT/FR2016/051262
§ 371 (c)(1),
(2) Date: Nov. 27, 2017

(87) PCT Pub. No.: WO2016/189260
PCT Pub. Date: Dec. 1, 2016

(65) Prior Publication Data
US 2018/0230119 A1    Aug. 16, 2018

(30) Foreign Application Priority Data
May 27, 2015   (FR) .................................... 15 54761

(51) Int. Cl.
*C07D 311/60*   (2006.01)
*A61K 31/352*   (2006.01)

(52) U.S. Cl.
CPC .......... *C07D 311/60* (2013.01); *A61K 31/352* (2013.01)

(58) Field of Classification Search
CPC .................................................... A61K 31/352
See application file for complete search history.

(56) References Cited

U.S. PATENT DOCUMENTS 4,105,675 A * 8/1978 Iacobucci ............ C07D 311/32
426/250
2014/0322371 A1* 10/2014 Veillet .................. A61K 31/191
424/776

FOREIGN PATENT DOCUMENTS

| FR | 2975008 A1 | 11/2012 |
| FR | 2996773 A1 | 4/2014 |
| WO | 2005/077176 A1 | 8/2005 |

OTHER PUBLICATIONS

Awika et al., Journal of Agricultural and Food Chemistry, 2004;52:4388-4394 (Year: 2004).*

(Continued)

*Primary Examiner* — San Ming R Hui
(74) *Attorney, Agent, or Firm* — Young & Thompson

(57) ABSTRACT

Disclosed is a method for the treatment, prevention and/or stabilisation of ARMD, Stargardt disease, pigmentary retinopathy and/or diabetic retinopathy, including the application of a 3-deoxyanthocyanidin of formula (I) in which $R^1$, $R^2$, $R^3$, $R^4$, $R^5$, $R^6$, $R^7$, $R^8$, $R^9$, $R^{10}$, $R^{11}$ and $X^-$ are as defined, with the condition that at least one of $R^1$, $R^2$, $R^3$, $R^4$ or $R^5$ is a hydroxyl and at least one of $R^8$, $R^9$, $R^{10}$ or $R^{11}$ is a hydroxyl.

7 Claims, 4 Drawing Sheets

(56) References Cited

OTHER PUBLICATIONS

Zafra-Stone et al., Mol. Nutr. Food Red., 2007;51:675-683 (Year: 2007).*

Sparrow et al., "Blue Light-Induced Apoptosis of A2E-Containing RPE: Involvement of Caspase-3 and Protection by Bcl-2", Investigative Ophthalmology & Visual Science, 2001, vol. 42, Issue 6, pp. 1356-1362.

Sparrow et al., "A2E-epoxides Damage DNA in Retinal Pigment Epithelial Cells", The Journal of Biological Chemistry, 2003, vol. 278, No. 20, pp. 18207-18213.

Liu et al., "Blueberry Anthocyanins: Protection Against Ageing and Light-Induced Damage in Retinal Pigment Epithelial Cells", British Journal of Nutrition, vol. 108, Issue 1, 2012, pp. 6-27.

Wang et al., "The Protective Effects of Berry-Derived Anthocyanins Against Visible Light-Induced Damage in Human Retinal Pigment Epithelial Cells", The Journal of the Science of Food and Agriculture, vol. 95, 2015, pp. 936-944.

Tanaka et al., "Purple Rice Extract and Anthocyanidins of the Constituents Protect Against Light-Induced Retinal Damage in Vitro and in Vivo", Journal of Agricultural Food Chemistry, vol. 59, 2011, pp. 528-536.

Tanaka et al., "Purple Rice Extract and its Constituents Suppress Endoplamic Reticulum Stress-Induced Retinal Damage in Vitro and in Vivo", Life Sciences, vol. 92, 2013, pp. 17-25.

Hanneken et al., "Flavonoids Protect Human Retinal Pigment Epithelial Cells from Oxidative-Stress-Induced Death", Investigative Ophthalmology & Visual Science, vol. 47, No. 7, 2006, pp. 3164-3177.

Majumdar et al., "Potential of the Biflavonoids in the Prevention/Treatment of Ocular Disorders", Journal of Pharmacy and Pharmacology, vol. 62, 2010, pp. 951-965.

Maeda et al., "Evaluation of Potential Therapies for a Mouse Model of Human Age-Related Macular Degeneration Caused by Delayed All-Trans-Retinal Clearance", Investigative Ophthalmology & Visual Science, vol. 50, No. 10, 2009, pp. 4917-4925.

Constantino et al, "Anthocyanidines as Inhibitors of Xanthine Oxidase", Pharmazie, vol. 50, No. H.8, 1995, pp. 573-574.

International Search Report issued Application No. PCT/FR2016/051262, dated Oct. 18, 2016.

* cited by examiner

USE OF 3-DEOXYANTHOCYANIDINS FOR TREATING OCCULAR DISEASES

FIELD OF THE INVENTION

This invention relates to the use of compounds of the flavonoid family, anthocyanidins, in particular 3-deoxyanthocyanidins, for the treatment, prevention and/or stabilisation of ocular diseases, in particular for the treatment, prevention and/or stabilisation of age-related macular degeneration (AMD), Stargardt disease, pigmentary retinopathy and/or diabetic retinopathy.

PRIOR ART

The accumulation of lipofuscins in retinal cells, such as the cells of the retinal pigment epithelium (RPE), is involved in various ocular diseases and appears during the course of ageing. The lipofuscins of the RPE cells include lipids, proteins and a heterogeneous mixture of fluorophores, in particular A2E (N-retinyl-N-retinylidene ethanolamine).

A2E is a by-product of visual cycle (FIG. 1), generated in the outer segment of the photoreceptors in the form of a precursor linked to a phospholipid. During visual cycle, the 11-cis-retinal is isomerised into all-trans-retinal under the effect of the light in the photoreceptors. The RPE cells make it possible to regenerate the 11-cis-retinal from the all-trans-retinal. In addition, RPE cells absorb and degrade on a daily basis a portion of the membranes of the outer segments of the photoreceptors in order to allow for the renewal of new discs at their base. However, the all-trans-retinal is not entirely regenerated into 11-cis-retinal, a portion is transformed into A2E by the condensation of two molecules of all-trans-retinal with ethanolamine. With age, the A2E accumulates progressively in the RPE cells.

It has been shown that the accumulation of lipofuscins in the RPE cells, in particular the accumulation of A2E, causes an increase in the death of the RPE cells. Indeed, under the action of the blue light and in the presence of oxygen, the A2E generates reactive species that cause damage to proteins, to lipids and to the DNA, and therefore substantial oxidative stress in the ageing RPE cells (Sparrow J R and Cai B., Invest Ophthalmol Vis Sci, 2001, 42, 1356-1362; Sparrow J R et al., J Biol Chem, 2003, 278(20), 18207-18213). The waste formed as such accumulates and ultimately causes from place to place the death of the RPE cells, followed by that of the photoreceptors to which they were associated.

Various ocular diseases are linked to the accumulation of lipofuscins in the RPE cells, such as for example AMD or Stargardt disease.

AMD is an evolving and debilitating chronic retinal degenerative disease, which affects the elderly subject and of which the origin is multifactorial. It is a cause of irreversible blindness in populations of the elderly, in particular in Europe and in North America.

AMD affects the central portion of the retina, called macula, resulting in a severe visual impairment and the irreversible loss of central vision. The pathophysiological mechanisms of AMD are still little understood, but it has been established that the progressive accumulation of lipofuscins, and the senescence of the RPE could be involved.

The early stage of AMD is marked by deposits, called Drusen deposits, which affect vision only marginally. The later phases of the disease include two severe forms of AMD: the dry form, also called geographic atrophy, and the wet form, also known under the name of exudative form or neovascular form. The dry form is more frequent than the wet form, but only the latter currently benefits from treatments.

Prevention or treatment attempts are currently based on dietary supplements that contain generic antioxidant compounds, such as for example zinc, vitamins A, C and E, with limited therapeutic efficacy.

There is therefore a need for new active compounds for the treatment, prevention and/or stabilisation of AMD, in particular dry AMD, but also for the treatment, prevention and/or stabilisation of ocular diseases linked to the accumulation of lipofuscins in the retinal cells such as Stargardt disease.

For this purpose, the use of anthocyanins coming from natural extracts was reported (Liu et al., British J. Nutr., 2012, 108, 16-27; Wang et al., J. Sci. Food Agric., 2015, 95, 936-944).

Anthocyanins belong to the class of polyphenolic compounds and are part of the pigments that are naturally present in fruits and flowers. The structure of these compounds comprises a flavylium cation linked to a glycoside (Scheme 1). In nature, anthocyanins are based on 6 different aglycones, linked to various sugars, with the most common being glucose, galactose and arabinose. The aglycone portion of anthocyanins is called anthocyanidin.

Scheme 1. General structure of natural anthocyanins, wherein R1-R5 are preferably H or OH.

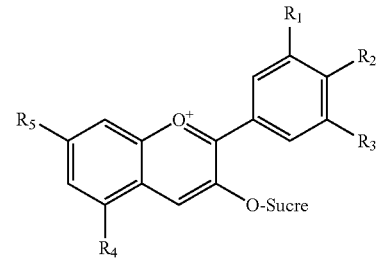

Sparrow et al. (WO2005/077176) also described the use of anthocyanins for the treatment or the prevention of ocular diseases linked to the accumulation of A2E in the RPE cells. The activity of certain anthocyanins was compared with their equivalent anthocyanidins. In particular, cyanidin, petunidin and malvidin (Table 1) were evaluated and showed photoprotection activities equivalent to those obtained for the corresponding anthocyanins, with cell survival of the RPE cells exposed to blue light ranging from 30 to 70% after incubation with 100 µM of compounds.

TABLE 1

Natural anthocyanidins tested for their photoprotective activity.

|  | $R_1$ | $R_2$ | $R_3$ |
|---|---|---|---|
| cyanidin | OH | OH | H |
| delphinidin | OH | OH | OH |
| malvidin | $OCH_3$ | OH | $OCH_3$ |

TABLE 1-continued

Natural anthocyanidins tested for their photoprotective activity.

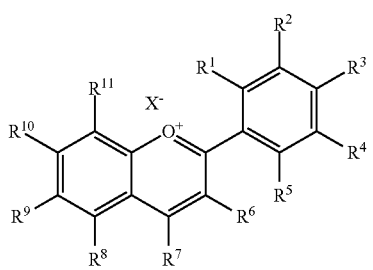

| | $R_1$ | $R_2$ | $R_3$ |
|---|---|---|---|
| peonidin | $OCH_3$ | OH | H |
| petunidin | OH | OH | $OCH_3$ |

Other studies have also showed that the use of natural anthocyanidins could have a photoprotective effect on the RPE cells (Tanaka et al., J. Agric. Food Chem., 2011, 59, 528-536; Tanaka et al., Life Sciences, 2013, 92, 17-25; FR2996773). In particular, cyanidin, delphinidin, peonidin and malvidin were evaluated in these studies. Cyanidin and delphinidin seem to have a photoprotective effect, contrary to malvidin. Contradicting results were obtained with regards to peonidin.

However, other studies have on the contrary concluded to the ineffectiveness of anthocyanidins for cell survival of the RPE cells, in particular for cyanidin, delphinidin, peonidin, petunidin and malvidin (Hanneken et al., Invest. Ophthal. Visual Sci., 2006; 47(7), 3164-3177; Majumdaar and Srirangam, J. Pharm. Pharmacol., 2010, 62, 951-965).

Prior art therefore gives contradictory results concerning the effectiveness of anthocyanidins in the photoprotection of the RPE cells.

Despite the existing negative prejudices, the Applicant conducted in-depth studies on the activity of natural and non-natural anthocyanidins for the photoprotection of the RPE cells.

Surprisingly, the Applicant found that the 3-deoxyanthocyanidins comprising at least one hydroxyl group on the cycle A and on the cycle B, have very good photoprotective activity. In particular, this invention relates to the use of 3-deoxyanthocyanidins of Formula I:

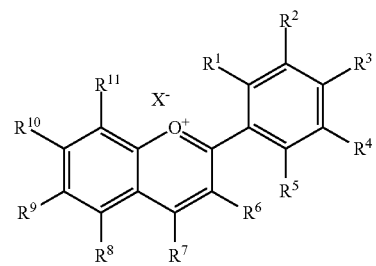

wherein $R^1$, $R^2$, $R^3$, $R^4$, $R^5$, $R^6$, $R^7$, $R^8$, $R^9$, $R^{10}$, $R^{11}$ and $X^-$ are as defined below, in particular $R^6$ is different from a hydroxyl, at least one of $R^1$, $R^2$, $R^3$, $R^4$ or $R^5$ is a hydroxyl and at least one of $R^8$, $R^9$, $R^{10}$ or $R^{11}$ is a hydroxyl; for the treatment, prevention and/or stabilisation of AMD, Stargardt disease, pigmentary retinopathy and/or diabetic retinopathy.

The Applicant showed that these compounds are effective in a cell model of phototoxicity induced by the association of a treatment by the A2E and of an illumination by blue light on primary cultures of RPE. The Applicant also showed that these compounds provide photoprotection in an in vivo model.

SUMMARY

The invention therefore relates to a compound of Formula I

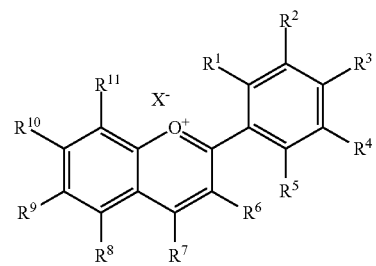

wherein
$R^1$, $R^2$, $R^3$, $R^4$ and $R^5$ each independently is a group selected from hydrogen, halo, hydroxyl, alkoxy, aryloxy, heteroaryloxy, acyloxy, alkyl, aryl, aralkyl, alkylaryl, alkenyl, nitro, nitrile, amino, with the condition that at least one of
$R^1$, $R^2$, $R^3$, $R^4$ or $R^5$ is a hydroxyl;
$R^6$ is a group selected from hydrogen, halo, alkoxy, aryloxy, heteroaryloxy, acyloxy, alkyl, aryl, aralkyl, alkylaryl, alkenyl, nitro, nitrile, amino;
$R^7$ is a group selected from hydrogen, halo, hydroxyl, alkoxy, aryloxy, heteroaryloxy, acyloxy, alkyl, aryl, aralkyl, alkylaryl, alkenyl, nitro, nitrile, amino;
$R^8$, $R^9$, $R^{19}$ and $R^{11}$ each independently is a group selected from hydrogen, halo, hydroxyl, alkoxy, aryloxy, heteroaryloxy, acyloxy, alkyl, aryl, aralkyl, alkylaryl, alkenyl, nitro, nitrile, amino, with the condition that at least one of $R^8$, $R^9$, $R^{19}$ or $R^{11}$ is a hydroxyl;
$X^-$ is an anion selected from: anion derived from a mineral acid such as for example a bromide, chloride, borotetrafluoride or perchloride anion; anion derived from an organic acid, such as for example an acetate, borate, citrate, tartrate, bisulphate, sulphate or phosphate anion; or an anion derived from a sulphate or sulphonate group;
for the use thereof in the treatment, prevention and/or stabilisation of AMD, Stargardt disease, pigmentary retinopathy and/or diabetic retinopathy.

According to an embodiment, in the compound of formula I, $R^6$ is a hydrogen atom.

According to an embodiment, the compound of formula I is of Formula Ia

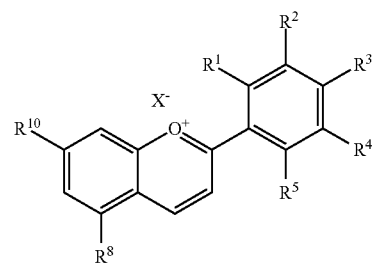

wherein $R^1$, $R^2$, $R^3$, $R^4$, $R^5$, $R^8$, $R^{10}$ and $X^-$ are as defined above.

According to an embodiment, in the compound of the invention, $R^1$, $R^2$, $R^3$, $R^4$ and $R^5$ each independently is a group selected from hydrogen, hydroxyl and alkoxy, with the condition that at least one of $R^1$, $R^2$, $R^3$, $R^4$ or $R^5$ is a hydroxyl; and $R^8$ and $R^{10}$ each independently is a group selected from hydrogen, hydroxyl and alkoxy, with the condition that at least one of $R^8$ or $R^{10}$ is a hydroxyl.

According to an embodiment, the compound of formula I is of Formula Ib

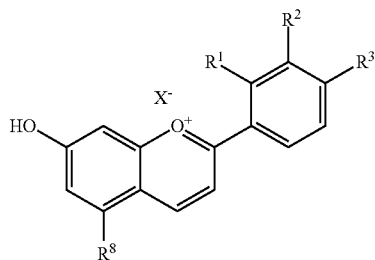

wherein $R^1$, $R^2$, $R^3$, $R^8$ and $X^-$ are such as defined hereinabove.

According to an embodiment, in the compound of the invention, $R^8$ is a hydrogen atom.

According to an embodiment, the compound for use according to the invention is selected from:
2',7-dihydroxy-4'-methoxy-flavylium chloride;
2',3',7-trihydroxy-4'-methoxy-flavylium chloride;
3',7-dihydroxy-4'-methoxy-flavylium chloride;
4',5,7-trihydroxy-flavylium chloride;
3',5,7-trihydroxy-4'-methoxy-flavylium chloride;
3',4',5',5,7-pentadroxy-flavylium chloride;
3',4',5,7-tetrahydroxy-flavylium chloride.

The invention also relates to a compound selected from:
2',7-dihydroxy-4'-methoxy-flavylium chloride;
2',3',7-trihydroxy-4'-methoxy-flavylium chloride.

The invention also relates to a pharmaceutical composition comprising a compound selected from 2',7-dihydroxy-4'-methoxy-flavylium chloride and 2',3',7-trihydroxy-4'-methoxy-flavylium chloride, in combination with a pharmaceutically acceptable carrier.

The invention also relates to a drug comprising a compound selected from 2',7-dihydroxy-4'-methoxy-flavylium chloride and 2',3',7-trihydroxy-4'-methoxy-flavylium chloride.

Definitions

In this invention, the terms hereinbelow are defined in the following way:

"acyloxy" relates to a —(C=O)—O-alkyl group.

"alkenyl" relates to any linear or branched hydrocarbon chain, optionally substituted, carrying at least one double bond, from 2 to 12 carbon atoms, preferably from 2 to 6 carbon atoms; such as for example vinyl or allyl.

"alkylaryl" relates to an alkyl-aryl-group.

"alkyl" relates to a saturated linear or branched hydrocarbon chain, from 1 to 12 carbon atoms, preferably from 1 to 6 carbon atoms, more preferably methyl, ethyl, propyl, isopropyl, n-butyl, sec-butyl, isobutyl, tert-butyl.

"alkoxy" relates to an —O-alkyl group.

"amino" refers to a —NH$_2$ group or to any group derived from —NH$_2$ by substitution of one or several hydrogen atoms with a substituted or unsubstituted, aliphatic or aromatic organic group. Preferably, the groups derived from —NH$_2$ are alkylamino groups i.e. N-alkyl groups, comprising the monoalkylamino and dialkylamino groups.

"aralkyl" relates to an aryl-alkyl-group.

"aryl" relates to a mono- or polycyclic system of 5 to 20, preferably from 6 to 12, carbon atoms that have one or several aromatic rings, among which can be mentioned the phenyl group, the biphenyl group, the 1-naphtyl group, the 2-naphtyl group, the tetrahydronaphtyl group, the indanyl group, and the binaphtyl group. The aryl group can be substituted with 1 to 3 substituents chosen independently of one another, from a hydroxyl group, a linear or branched alkyl group comprising 1, 2, 3 4, 5 or 6 carbon atoms, in particular methyl, ethyl, propyl, butyl, an alkoxy group or a halogen atom, in particular bromine, chlorine and iodine.

"aryloxy" relates to an —O-aryl group.

"halo" refers to fluoro, chloro, bromo, or iodo.

"heteroaryl" relates to a mono- or polycyclic group of 5 to 20, preferably from 5 to 12, carbon atoms that have one or several aromatic rings, wherein one or several carbon atoms are replaced with a heteroatom, preferably N, O or S, with the heteroatoms of nitrogen and sulphur able to optionally be oxidised and with the heteroatoms of nitrogen able to optionally be quaternised. Such cycles can be condensed to an aryl, cycloalkyl, heteroaryl or heterocyclyl group. Non-limiting examples of such a heteroaryl group are the following: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo [2,1-b] [1, 3] thiazolyl, thieno [3,2-b] furanyl, thieno [3,2-b] thiophenyl, thieno [2,3-d] [1, 3] thiazolyl, thieno [2,3-d] imidazolyl, tetrazolo [1,5-a] pyridinyl, indolyl, indolizinyl, iso-indolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1, 2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo [1,2-a] pyridinyl, a 6-oxo-pyridazine-1 (6H)-yl, 2-oxo-pyridine-1 (2H)-yle, 6-oxo-pyrudazin-1(6H)-yl, 2-oxo-pyridine-1 (2H)-yl, 1,3-benzodioxolyl, quinolinyl, isoquinolinyl, cinnolinyl, quinazolinyl, quinoxalinyle.

"heteroaryloxy" relates to an —O-heteroaryl group.

"subject" refers to an animal, including a human being. In terms of this invention, a subject can be a "patient", namely a person receiving medical care, undergoing or having undergone medical treatment, or monitored for the development of a disease.

"treatment" means preventing, reducing or attenuating at least one undesirable effect or symptom of a disease.

"prevention of a disease" means preventing the occurrence of at least one undesirable effect or symptom of a disease. In this invention, the term "prevention" can refer to a secondary prevention, namely the prevention of the reappearance of a symptom or of a relapse of the disease.

"stabilise a disease" means the stopping or the slowing down of the aggravation of at least one undesirable effect or symptom of a disease. It can also refer to the action of reducing the consequences of a disease once established.

"effective amount" refers to the amount of active agent that is required and sufficient to slow down or stop the progression, the aggravation or the deterioration of one or several symptoms of a disease or of the disorder; or the symptoms relief of a disease or of a condition; or curing the disease or disorder.

"pharmaceutically acceptable carrier" refers to an excipient that does not produce any undesirable, allergic or other reaction, when it is administered to an animal, preferably to a human being. It includes all of the solvents, dispersion mediums, coatings, antibacterial and antifungal agents, isotonic agents, absorption retarding agents and similar compounds. For human administration, the preparations must meet standards of sterility, general safety and purity such as required by the regulatory offices, such as, for example, the FDA or EMA.

"administration" means to provide the active agent, alone or as part of a pharmaceutically acceptable composition, to the subject wherein a symptom or the disease must be treated or prevented.

DETAILED DESCRIPTION

Compounds

This invention relates to 3-deoxyanthocyanidins of Formula I

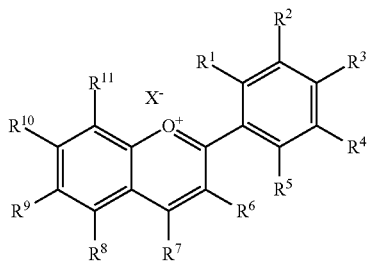

wherein
$R^1$, $R^2$, $R^3$, $R^4$ and $R^5$ each independently is a group selected from hydrogen, halo, hydroxyl, alkoxy, aryloxy, heteroaryloxy, acyloxy, alkyl, aryl, aralkyl, alkylaryl, alkenyl, nitro, nitrile, amino, with the condition that at least one of $R^1$, $R^2$, $R^3$, $R^4$ or $R^5$ is a hydroxyl;
$R^6$ is a group selected from hydrogen, halo, alkoxy, aryloxy, heteroaryloxy, acyloxy, alkyl, aryl, aralkyl, alkylaryl, alkenyl, nitro, nitrile, amino;
$R^7$ is a group selected from hydrogen, halo, hydroxyl, alkoxy, aryloxy, heteroaryloxy, acyloxy, alkyl, aryl, aralkyl, alkylaryl, alkenyl, nitro, nitrile, amino;
$R^8$, $R^9$, $R^{19}$ and $R^{11}$ each independently is a group selected from hydrogen, halo, hydroxyl, alkoxy, aryloxy, heteroaryloxy, acyloxy, alkyl, aryl, aralkyl, alkylaryl, alkenyl, nitro, nitrile, amino, with the condition that at least one of $R^8$, $R^9$, $R^{19}$ or $R^{11}$ is a hydroxyl;
$X^-$ is an anion selected from: anion derived from a mineral acid such as for example a bromide, chloride, borotetrafluoride or perchloride anion; anion derived from an organic acid, such as for example an acetate, borate, citrate, tartrate, bisulphate, sulphate or phosphate anion; or an anion derived from a sulphate or sulphonate group.

In a particular embodiment, $R^1$, $R^2$, $R^3$, $R^4$ and $R^5$ each independently is a group selected from hydrogen, hydroxyl, alkoxy, aryloxy, heteroaryloxy, acyloxy, with the condition that at least one of $R^1$, $R^2$, $R^3$, $R^4$ or $R^5$ is a hydroxyl, preferably with the condition that at least one of $R^1$, $R^2$ or $R^3$ is a hydroxyl.

In a particular embodiment, $R^1$, $R^2$, $R^3$, $R^4$ and $R^5$ each independently is a group selected from hydrogen, hydroxyl, alkoxy, with the condition that at least one of $R^1$, $R^2$, $R^3$, $R^4$ or $R^5$ is a hydroxyl, preferably with the condition that at least one of $R^1$, $R^2$ or $R^3$ is a hydroxyl. Preferably, the alkoxy group is a methoxy group.

In a particular embodiment, $R^1$, $R^2$, $R^3$, $R^4$ and $R^5$ each independently is a group selected from hydrogen, hydroxyl, methoxy, with the condition that at least one of $R^1$, $R^2$, $R^3$, $R^4$ or $R^5$ is a hydroxyl, preferably with the condition that at least one of $R^1$, $R^2$ or $R^3$ is a hydroxyl.

In a particular embodiment, $R^1$ is a hydrogen or a hydroxyl, preferably $R^1$ is a hydrogen.

In a particular embodiment, $R^1$ is a hydrogen or a hydroxyl.

In a particular embodiment, $R^3$ is a hydroxyl or an alkoxy. In a particular embodiment, $R^3$ is a hydroxyl. In a particular embodiment, $R^3$ is an alkoxy, preferably methoxy.

In a particular embodiment, $R^4$ is a hydrogen. In a particular embodiment, $R^5$ is a hydrogen. In a particular embodiment, $R^4$ and $R^5$ are hydrogens.

In a particular embodiment, $R^6$ is a hydrogen, alkyl, alkoxy or aryl. In a particular embodiment, $R^6$ is a hydrogen.

In a particular embodiment, $R^7$ is a hydrogen, a hydroxyl or an alkoxy, preferably $R^7$ is a hydrogen.

In a particular embodiment, $R^8$, $R^9$, $R^{19}$ and $R^{11}$ each independently is a group selected from hydrogen, hydroxyl, alkoxy, aryloxy, heteroaryloxy, acyloxy, with the condition that at least one of $R^8$, $R^9$, $R^{10}$ or $R^{11}$ is a hydroxyl, preferably with the condition that at least $R^8$ or $R^{19}$ is a hydroxyl.

In a particular embodiment, $R^8$, $R^9$, $R^{19}$ and $R^{11}$ each independently is a group selected from hydrogen, hydroxyl, alkoxy, with the condition that at least one of $R^8$, $R^9$, $R^{19}$ or $R^{11}$ is a hydroxyl, preferably with the condition that at least $R^8$ or $R^{10}$ is a hydroxyl. Preferably, the alkoxy group is a methoxy group.

In a particular embodiment, $R^8$, $R^9$, $R^{19}$ and $R^{11}$ each independently is a group selected from hydrogen, hydroxyl, with the condition that at least one of $R^8$, $R^9$, $R^{10}$ or $R^{11}$ is a hydroxyl, preferably with the condition that at least $R^8$ or $R^{19}$ is a hydroxyl.

In a particular embodiment, $R^8$ is a hydrogen, a hydroxyl or an alkoxy. In a particular embodiment, $R^8$ is a hydrogen. In a particular embodiment, $R^8$ is a hydroxyl. In a particular embodiment, $R^6$ and $R^8$ are hydrogens.

In a particular embodiment, $R^9$ is a hydrogen, a hydroxyl or an alkoxy. In a particular embodiment, $R^9$ is a hydrogen.

In a particular embodiment, $R^{10}$ is a hydrogen, a hydroxyl or an alkoxy. In a particular embodiment, $R^{10}$ is a hydroxyl.

In a particular embodiment, $R^{11}$ is a hydrogen, a hydroxyl or an alkoxy. In a particular embodiment, $R^{11}$ is a hydrogen.

In a particular embodiment, $R^9$ and $R^{11}$ are hydrogens. In a particular embodiment, $R^8$, $R^9$ and $R^{11}$ are hydrogens.

In a particular embodiment, $R^8$ and $R^{10}$ are hydroxyls.

In a particular embodiment, $R^8$, $R^9$ and $R^{11}$ are hydrogens and $R^{10}$ is a hydroxyl. According to a particular embodiment, $R^9$ and $R^{11}$ are hydrogens and $R^8$ and $R^{10}$ are hydroxyls.

In a particular embodiment, $X^-$ is an anion derived from a mineral acid such as for example a bromide, chloride, borotetrafluoride or perchloride anion; preferably $X^-$ is a chloride or a bromide; more preferably $X^-$ is a chloride.

In a particular embodiment, $X^-$ is an anion derived from an organic acid, such as for example an acetate, borate, citrate, tartrate, bisulphate, sulphate or phosphate anion.

In a particular embodiment, $X^-$ is an anion derived from a sulphate or sulphonate group.

According to an embodiment, the compound of Formula I is of Formula I'

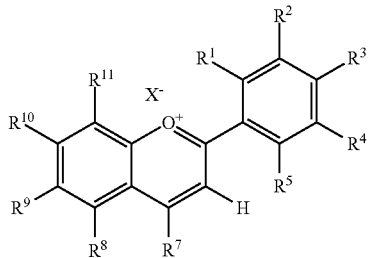

wherein $R^1$, $R^2$, $R^3$, $R^4$, $R^5$, $R^7$, $R^8$, $R^9$, $R^{10}$, $R^{11}$ and $X^-$ are such as defined in formula I.

According to an embodiment, the compound of Formula I is of Formula Ia

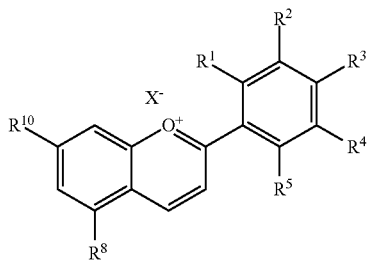

wherein $R^1$, $R^2$, $R^3$, $R^4$, $R^5$, $R^8$, $R^{10}$ and $X^-$ are such as defined hereinabove.

According to a particular embodiment, in the Formula Ia:

$R^1$, $R^2$, $R^3$, $R^4$ and $R^5$ each independently is a group selected from hydrogen, hydroxyl and alkoxy, with the condition that at least one of $R^1$, $R^2$, $R^3$, $R^4$ or $R^5$ is a hydroxyl;

$R^8$ and $R^{10}$ each independently is a group selected from hydrogen, hydroxyl and alkoxy, with the condition that at least one of $R^8$ or $R^{10}$ is a hydroxyl.

According to an embodiment, the compound of Formula I is of Formula Ib

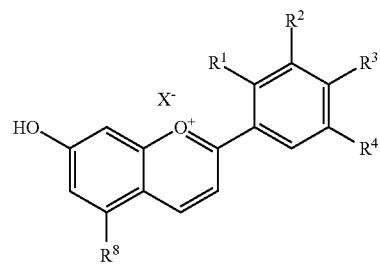

wherein $R^1$, $R^2$, $R^3$, $R^4$, $R^8$ and $X^-$ are such as defined hereinabove.

According to a particular embodiment, in the Formula Ib:

$R^1$, $R^2$, $R^3$ and $R^4$ each independently is a group selected from hydrogen, hydroxyl and alkoxy, with the condition that at least one of $R^1$, $R^2$, $R^3$ or $R^4$ is a hydroxyl;

$R^8$ is a group selected from hydrogen, hydroxyl and alkoxy.

According to a particular embodiment, in the Formula Ib:

$R^1$, $R^2$, $R^3$ and $R^4$ each independently is a group selected from hydrogen, hydroxyl and methoxy, with the condition that at least one of $R^1$, $R^2$, $R^3$ or $R^4$ is a hydroxyl;

$R^8$ is a hydrogen or a hydroxyl.

According to an embodiment, the compounds of Formula I are those listed in the table hereinbelow:

| Compound No. | Structure | Name |
|---|---|---|
| 1 | ![structure] | 2',7-dihydroxy-4'-methoxy-flavylium chloride |
| 2 | ![structure] | 2',3',7-trihydroxy-4'-methoxy-flavylium chloride |

-continued

| Compound No. | Structure | Name |
|---|---|---|
| 3 | 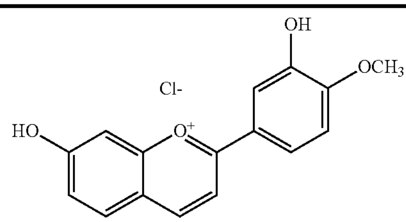 | 3',7-dihydroxy-4'-methoxy-flavylium chloride |
| 4 | 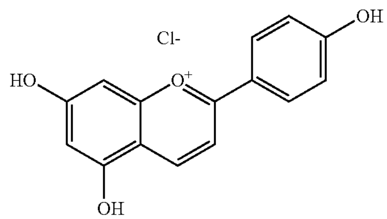 [SMILES: Oc1ccc(-c2ccc3c(O)cc(O)cc3[o+]2)cc1 ; [Cl-]] | 4',5,7-trihydroxy-flavylium chloride (apigeninidin) |
| 5 | 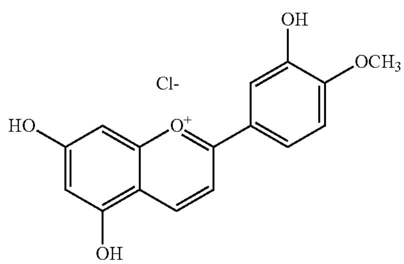 [SMILES: COc1ccc(-c2ccc3c(O)cc(O)cc3[o+]2)cc1O ; [Cl-]] | 3',5,7-trihydroxy-4'-methoxy-flavylium chloride (diosmetinidin) |
| 6 | 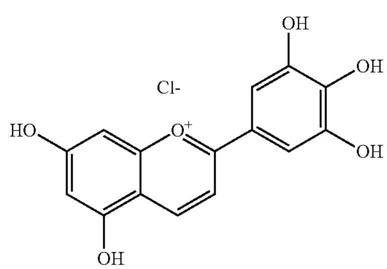 [SMILES: Oc1cc(O)c2ccc(-c3cc(O)c(O)c(O)c3)[o+]c2c1 ; [Cl-]] | 3',4',5',5,7-pentadroxy-flavylium chloride (tricetinidin) |
| 7 | 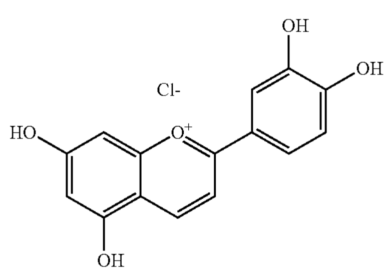 [SMILES: Oc1cc(O)c2ccc(-c3ccc(O)c(O)c3)[o+]c2c1 ; [Cl-]] | 3',4',5,7-tetrahydroxy-flavylium chloride (luteolinidin) |

According to a particular embodiment, the compounds of Formula I are the compounds no. 1 and 2.

According to an embodiment, the compound of Formula I is a compound of natural origin, such as for example apigeninidin, diosmetinidin, tricetinidin or luteolidin. The compounds of natural origin can be extracted from natural products, in particular from plants and/or fruits, or be obtained by chemical synthesis, whether by total synthesis or by hemi-synthesis using natural compounds, such as for example the corresponding anthocyanins.

According to another embodiment, the compound of Formula I is a non-natural compound. The non-natural compounds can be obtained by chemical synthesis, either by total synthesis or by hemi-synthesis.

The compounds of Formula I can be prepared by reactions known to those skilled in the art.

Uses

The invention relates to a composition comprising a compound of Formula I and a physiologically acceptable carrier. According to an embodiment, the composition of the invention is a pharmaceutical composition comprising a compound of Formula I in combination with a pharmaceutically acceptable carrier.

The invention relates to a drug comprising a compound of Formula I.

The uses described hereinbelow relate to the use of a compound of Formula I, of a pharmaceutical composition or of a drug according to this invention.

This invention relates to the use of compounds of Formula I, for the treatment, prevention and/or stabilisation of ocular diseases. According to an embodiment, the invention relates to the use of compounds of Formula I, for the treatment, prevention and/or stabilisation of ocular diseases linked to the accumulation of lipofuscins in the retinal cells, in particular for the treatment, prevention and/or stabilisation of AMD or Stargardt disease.

According to an embodiment, the invention relates to the use of compounds of Formula I, for the treatment, prevention and/or stabilisation of AMD, Stargardt disease, pigmentary retinopathy and/or diabetic retinopathy.

According to an embodiment, the invention relates to the use of compounds of Formula I for the treatment, prevention and/or stabilisation of AMD. According to a particular embodiment, the invention relates to the use of compounds of Formula I for the treatment, prevention and/or stabilisation of intermediate forms of AMD. The term "intermediate form" refers to the early stage of AMD, marked by deposits called Drusen deposits, which affect vision only marginally. According to a particular embodiment, the invention relates to the use of compounds of Formula I for the treatment, prevention and/or stabilisation of severe forms of AMD, in particular the dry and/or wet forms of AMD. According to a particular embodiment, the invention relates to the use of compounds of Formula I for the treatment, prevention and/or stabilisation of dry AMD. According to a particular embodiment, the invention relates to the use of compounds of Formula I for the treatment, prevention and/or stabilisation of wet AMD.

According to an embodiment, the invention relates to the use of compounds of Formula I for the treatment, prevention and/or stabilisation of Stargardt disease.

According to an embodiment, the invention relates to the use of compounds of Formula I for the treatment, prevention and/or stabilisation of pigmentary retinopathy.

According to an embodiment, the invention relates to the use of compounds of Formula I for the treatment, prevention and/or stabilisation of diabetic retinopathy.

The invention also relates to the use of compounds of Formula I for preventing the damages that can be caused to the retina by exposure to blue radiation. The term "blue radiation" means the radiation corresponding to the blue band of the visible light spectrum, i.e. a wavelength between 435 and 490 nm.

According to an embodiment, the invention relates to the use of compounds of Formula I to reduce cell death of the retinal pigment epithelium (RPE).

According to an embodiment, the invention relates to the use of compounds of Formula I to reduce or prevent the accumulation of lipofuscin in the RPE cells. In an embodiment, lipofuscin comprises A2E and/or isomeric or oxidised forms of A2E.

According to an embodiment, the invention relates to the use of compounds of Formula I to stabilise the RPE cell membranes. In an embodiment, the cell membranes can be plasma, lysosomal, nuclear or mitochondrial membranes.

According to an embodiment, the uses mentioned hereinabove relate to a compound or a mixture of compounds of Formula I.

According to an embodiment, the uses mentioned hereinabove relate to one or several compounds of Formula I in combination with another active agent. In particular, the active agent can be an antioxidant, such as for example zinc or vitamins A, C or E.

The invention also relates to a method for treating and/or preventing an ocular disease comprising the administration to a subject of a compound of Formula I according to the invention in an effective amount to improve and/or prevent said ocular disease. According to an embodiment, the invention relates to a method for the treatment, prevention and/or stabilisation of an ocular disease linked to the accumulation of lipofuscins in the retinal cells, more particularly for the treatment, prevention and/or stabilisation of AMD or Stargardt disease; comprising the administration to a subject of a compound of Formula I according to the invention in an effective amount to improve and/or prevent said ocular disease.

According to an embodiment, the invention relates to a method for treating and/or preventing AMD, Stargardt disease, pigmentary retinopathy and/or diabetic retinopathy.

The invention also relates to the use of compounds of Formula I for the preparation of a drug for the treatment, prevention and/or stabilisation of an ocular disease. According to an embodiment, the invention relates to the use of compounds of Formula I for the preparation of a drug for the treatment, prevention and/or stabilisation of an ocular disease linked to the accumulation of lipofuscins in the retinal cells, more particularly for the treatment, prevention and/or stabilisation of AMD or Stargardt disease.

According to an embodiment, the invention relates to the use of compounds of Formula I for the preparation of a drug for the treatment, prevention and/or stabilisation of AMD, Stargardt disease, pigmentary retinopathy and/or diabetic retinopathy.

According to an embodiment, the subject is an animal, preferably a mammal, more preferably a human.

According to an embodiment, the patient is diagnosed with AMD, Stargardt disease, pigmentary retinopathy and/or diabetic retinopathy. According to another embodiment, the subject is at a risk of developing AMD, Stargardt disease, pigmentary retinopathy and/or diabetic retinopathy. According to an embodiment, the subject has a genetic predisposition for developing AMD, Stargardt disease, pigmentary retinopathy and/or diabetic retinopathy.

According to an embodiment, the compounds of Formula I of the invention are administered by intraocular route. The term "intraocular route" refers to an administration of the compound directly inside the eye. The inside of the eye includes in particular the anterior chamber, the posterior chamber, the vitreous, the choroid, the macula, the retina, the blood vessels and the nerves that vascularise or innervate the posterior region of the eye. According to an embodiment, the compounds of Formula I are administered by intraocular route in the posterior segment of the eye. According to an embodiment, the compounds of Formula I are administered intravitreously. According to another embodiment, the compounds of Formula I are administered in the subretinal compartment of the eye. According to another embodiment, the compounds of Formula I are administered subconjunctivally.

According to an embodiment, the compounds of Formula I are administered topically. Drops or baths can be used. Iontophoresis methods known to those skilled in the art can also be used in order to favour the topical absorption of the compounds of the invention into the eye.

According to an embodiment, the compounds of Formula I are not administered orally.

According to an embodiment, the compounds of Formula I are formulated in a form that can be injected. In an embodiment, the compounds of Formula I are formulated in the form of a solution, such as for example a sterile aqueous solution, a dispersion, an emulsion, a suspension; or in a solid form that is suitable for the preparation of a solution or of a suspension by the adding of a liquid.

According to an embodiment, the compounds of Formula I are formulated in such a way that a sustained and/or controlled release can occur. In particular, the compounds of Formula I can be formulated in the form of an implant or in a bioresorbable matrix. The bioresorbable matrix can include a carbomer or a polymer. The polymer can be a biodegradable microsphere. The compounds of Formula I can alternatively be formulated in the form of liposomes. Any ocular formulation that makes it possible to obtain a sustained and/or controlled release of the active substance known to those skilled in the art can be used.

According to an embodiment, the compounds of Formula I are administered at a frequency of at most once a month, preferably once every 2 months, more preferably once every 4 months, even more preferably once every 6 months.

According to an embodiment, the compounds of Formula I are administered intravitreously in a form that allows for the daily release of a dose ranging from 0.01 mg to 1 mg per eye, preferably 0.1 mg to 0.5 mg per eye.

EXAMPLES

Figure 1:
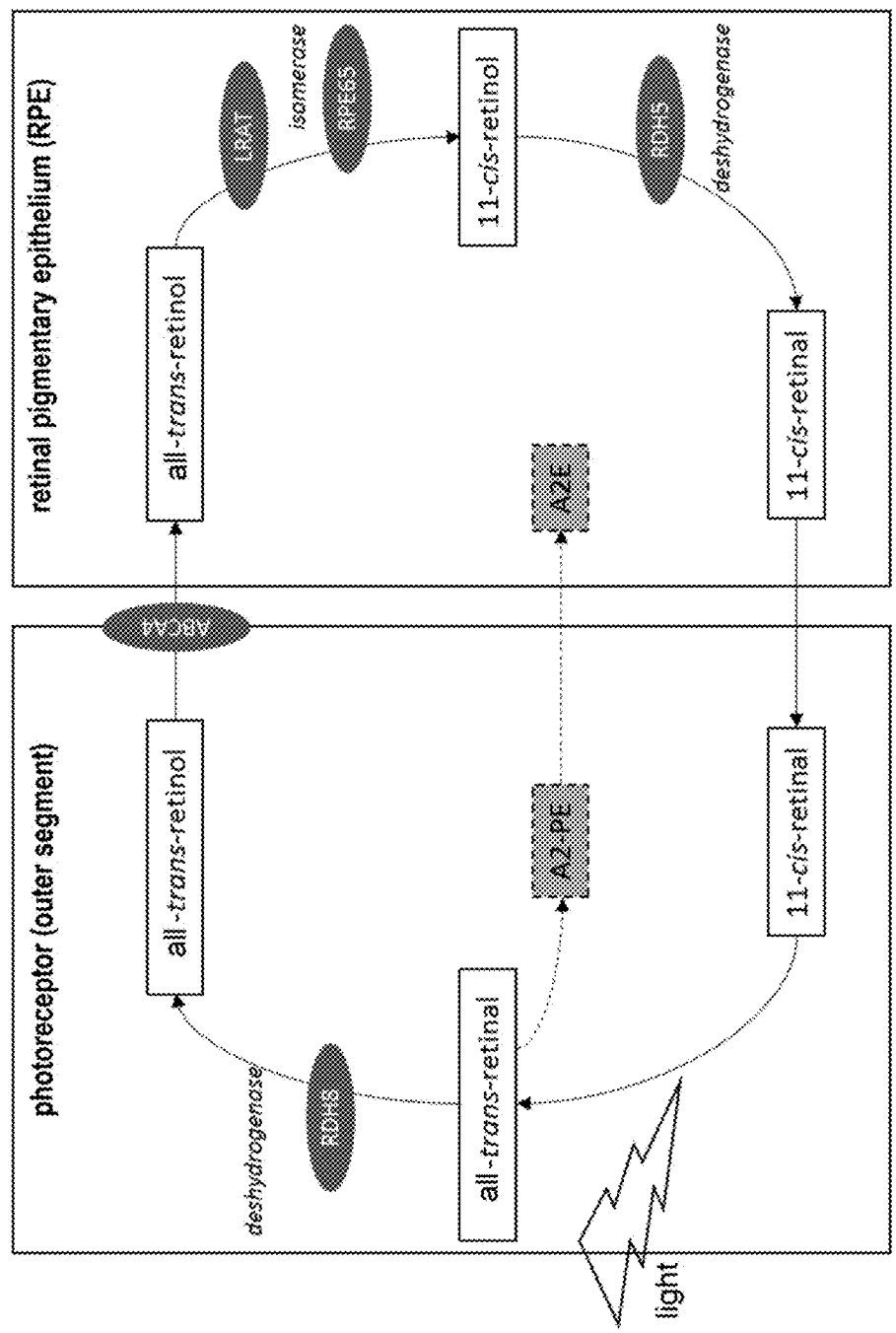
FIG. 1 is a scheme that summarises the main steps of visual cycle.

This invention shall be better understood when reading the following examples which show the invention in a non-limiting manner.

Example 1: Synthesis of the Compounds of the Invention

Compound 1. The 2,4-dihydroxybenzaldehyde (69 mg) and the 2'-hydroxy-4'-methoxy-acetophenone (83 mg-1 equivalent) are brought into solution in 500 μL of ethanol. 40 μL of thionyl chloride are added directly into the reaction medium which quickly becomes highly coloured. After one hour of stirring, the reaction medium is evaporated and the residue is precipitated in ethyl acetate, filtered and dried in order to yield the final compound (77 mg-yield 50%).

Compound 2. The 2,4-dihydroxybenzaldehyde (276 mg) and the 2',3'-dihydroxy-4'-methoxy-acetophenone (364 mg-1 equivalent) are brought into solution in 2 mL of ethanol and 2 mL of ethyl acetate. 500 μL of thionyl chloride are added directly into the reaction medium which quickly becomes highly coloured. After one hour of stirring, the reaction medium is evaporated and the residue is precipitated in ethyl acetate, filtered and dried. The solid is brought into solution in a minimum of methanol and is precipitated by the adding of an equivalent volume of tertio-butyl-methyl-ether (TBME). The solid is filtered and dried. The procedure is repeated until the purity is correct. The final yield is 60%.

The compounds obtained have purities>95% (HPLC) and their identity was confirmed by MS and NMR spectroscopy. The high-resolution mass spectrums were carried out on a LTQ Orbitrap-XL spectrometer (ThermoFisher Scientific), equipped with an NSI source (nano-ESI). The nuclear magnetic resonance spectrums (NMR) of the proton ($^1H$) were carried out in the DMSO-$d_6$+1% $CF_3COOD$ on a Bruker Avance DPX300 device (300.16 MHz).

HRMS (Orbitrap).

Compound 1. m/z 269.0809 (M)+, calc. 269.0808 for $C_{16}H_{13}O_4$, $\Delta=0.054$ ppm.

Compound 2. m/z 285.0757 (M)+, calc. 285,0757 for $C_{16}H_{13}O_5$, $\Delta=-0.105$ ppm.

$^1H$-NMR spectrums (δ ppm)

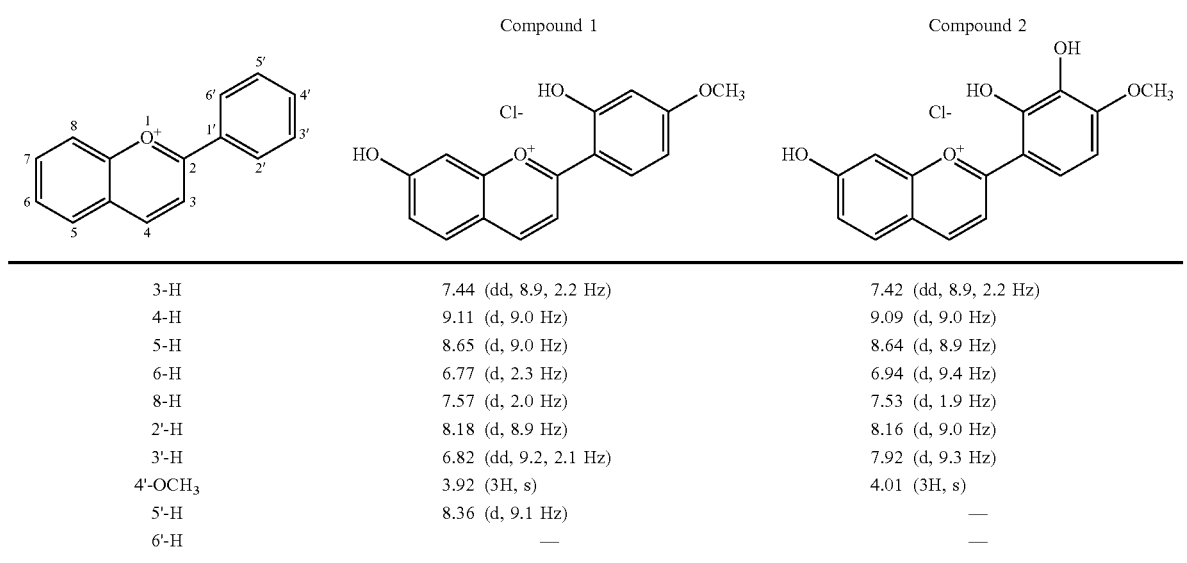

| | Compound 1 | Compound 2 |
|---|---|---|
| 3-H | 7.44 (dd, 8.9, 2.2 Hz) | 7.42 (dd, 8.9, 2.2 Hz) |
| 4-H | 9.11 (d, 9.0 Hz) | 9.09 (d, 9.0 Hz) |
| 5-H | 8.65 (d, 9.0 Hz) | 8.64 (d, 8.9 Hz) |
| 6-H | 6.77 (d, 2.3 Hz) | 6.94 (d, 9.4 Hz) |
| 8-H | 7.57 (d, 2.0 Hz) | 7.53 (d, 1.9 Hz) |
| 2'-H | 8.18 (d, 8.9 Hz) | 8.16 (d, 9.0 Hz) |
| 3'-H | 6.82 (dd, 9.2, 2.1 Hz) | 7.92 (d, 9.3 Hz) |
| 4'-OCH$_3$ | 3.92 (3H, s) | 4.01 (3H, s) |
| 5'-H | 8.36 (d, 9.1 Hz) | — |
| 6'-H | — | — |

Example 2: In Vitro Assay of the Photoprotective Activity

Method

A cell model of phototoxicity induced by the association of a treatment by the A2E and of an illumination by blue light on primary cultures of RPE, wherein cell survival was measured, was used. This model uses primary cultures of retinal pigment epithelium of adult pigs.

This model makes it possible in particular to carry out the screening of molecules aimed at the discovery of new candidates for a treatment of the dry form of AMD. This model is closer to the "physiological" situation than the cell lines commonly used in literature, because the cells used contain protective substances provided by the diet of the animal and are therefore not in a situation of "deficiency", and their disturbance is caused by the adding of A2E into the culture medium.

The cell cultivated in 96-well plates were treated for 48 hours with the compounds to be tested (in a 5 mM solution in the DMSO) in such a way as to obtain final concentrations of 5 or 20 µM), of which the last 19 hours in the presence of A2E (final concentration 30 µM). The pre-treated cells are then illuminated for 50 min with blue light (470 nm) provided by the 96 LED W7113PBC/H (Kingbright) with a beam angle of 16°, beaming 1440 mcd (millicandela) under a current of 8.6 mA. Cell survival is measured after 24 hours.

Cell survival and death are detected 24 hours after the induction of the phototoxicity by colouration of the cells with Hoechst (a nuclear marker) and with ethidium (a marker of the nuclei of dead cells). Images of each well are acquired on a fluorescent microscope equipped with a motorised stage controlled by the Metamorph software, and cell survival is quantified by a dedicated quantification program. The experiments are conducted on 96-well microplates in quadruplicate and each experiment is reproduced at least four times.

The results are expressed in the form of a ratio representing the number of living cells in the wells treated by the molecules to be tested divided by the number of living cells in the control wells (treated with the dilution medium without A2E) and multiplied by 100. The value of the controls treated with A2E but without the molecule is 39.7±3.7.

Results

The compounds of the invention make it possible to obtain very high cell survival percentages, at 20 µM as well as at 5 µM (Table 2).

TABLE 2

Cell survival: compounds of the invention.

| Compounds | 20 µM | 5 µM |
|---|---|---|
| 1 | 89.9 ± 4.9 | NA |
| 2 | 86.7 ± 2.3 | NA |
| 3 | 77.0 ± 2.7 | NA |
| 4 | 89.5 ± 3.5 | 71 ± 3.6 |
| 5 | 90.8 ± 3.6 | 84.5 ± 1.4 |
| 6 | 99.3 ± 3.3 | 74.9 ± 4.2 |
| 7 | 93.6 ± 6.7 | 72 ± 4.4 |

NA: not available

For comparison, 3-hydroxy-anthocyanidins were tested (Table 3).

TABLE 3

3-hydroxy-anthocyanidins tested.

| | $R_1$ | $R_2$ | $R_3$ | $R_4$ | $R_5$ |
|---|---|---|---|---|---|
| cyanidin | OH | H | OH | H | H |
| delphinidin | OH | OH | OH | H | H |
| fisetinidin | H | OH | H | H | H |
| gossypetinidin | H | OH | OH | H | OH |
| guibourtinidin | H | H | H | H | H |
| malvidin | $OCH_3$ | $OCH_3$ | OH | H | H |
| peonidin | $OCH_3$ | H | OH | H | H |
| petunidin | OH | $OCH_3$ | OH | H | H |
| quercetagetinidin | OH | H | OH | OH | H |

The results of cell survival in the presence of 3-hydroxy-anthocyanidins are reported in table 4.

TABLE 4

Cell survival: 3-hydroxy-anthocyanidins.

| Compounds | 20 µM | 5 µM |
|---|---|---|
| Cyanidin | 92.9 ± 1.9 | 56.4 ± 8.8 |
| Delphinidin | 57.8 ± 5.6 | 40.5 ± 6.2 |
| Fisetinidin | 39.3 ± 3.2 | NA |
| Gossypetinidin | 36.5 ± 14.4 | NA |
| Guibourtinidin | 42.8 ± 6.9 | NA |
| Malvidin | 51.5 ± 6.9 | NA |
| Peonidin | 60.4 ± 8.5 | NA |
| Petunidin | 67.2 ± 6.9 | NA |
| Quercetagetinidin | 54.3 ± 6.6 | NA |

These results show that the presence of a hydroxyl group in position 3 of the anthocyanidins substantially reduces the effectiveness of the photoprotection. Only cyanidin has a substantial photoprotector effect at 20 µM. However, at a lower concentration, its effectiveness is substantially reduced, contrary to the compounds of the invention.

For comparison, 3-deoxy-anthocyanidins that do not carry at least one free hydroxyl on the cycle A and on the cycle B were also tested (Table 5).

TABLE 5

Cell survival: 3-deoxy-anthocyanidins not carrying at least one hydroxyl on the cycle A or on the cycle B.

| Compounds | 20 µM | 5 µM |
|---|---|---|
| 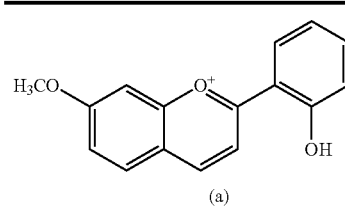 (a) | 39.2 ± 7.4 | NA |

TABLE 5-continued

Cell survival: 3-deoxy-anthocyanidins not carrying
at least one hydroxyl on the cycle A or on the cycle B.

| Compounds | 20 μM | 5 μM |
|---|---|---|
| (b) | 48.7 ± 5.5 | NA |
| (c) | 46.1 ± 4.7 | NA |

The percentages of cell survival obtained at 20 μM are less than 50%; the concentration 5 μM was therefore not tested.

The results obtained clearly show that when there is not at least one hydroxyl group on each one of the cycles A and B, the efficacy of the photoprotection is much less substantial than with the compounds of the invention.

Example 3: In Vivo Assay of the Photoprotective Activity in Mice

A genetically modified mouse model developed by Maeda et al. (Invest Ophthalmol. Vis. Sci., 2009, 50, 4917-4925) was used to test the photoprotective activity of the compounds of the invention.

In this mouse model, two genes involved in the visual pigment cycle (ABCA4 and Rdh8, see FIG. 1) are inactivated, which results in an early accumulation of A2E in the eyes. This animal model is therefore representative of the human pathology.

Mice aged 7 weeks were used to carry out the unilateral intravitreal injections of solubilised diosmetinidin (50 μM) in DMSO and diluted in PBS (1.2:100), in order to obtain a concentration in the vitreous of 100-130 μM. DMSO diluted in the PBS was injected into the control animals. After 24 h in the dark, the mice were subjected to an exposure to blue light (4000 lux, 1 h).

Figure 2:
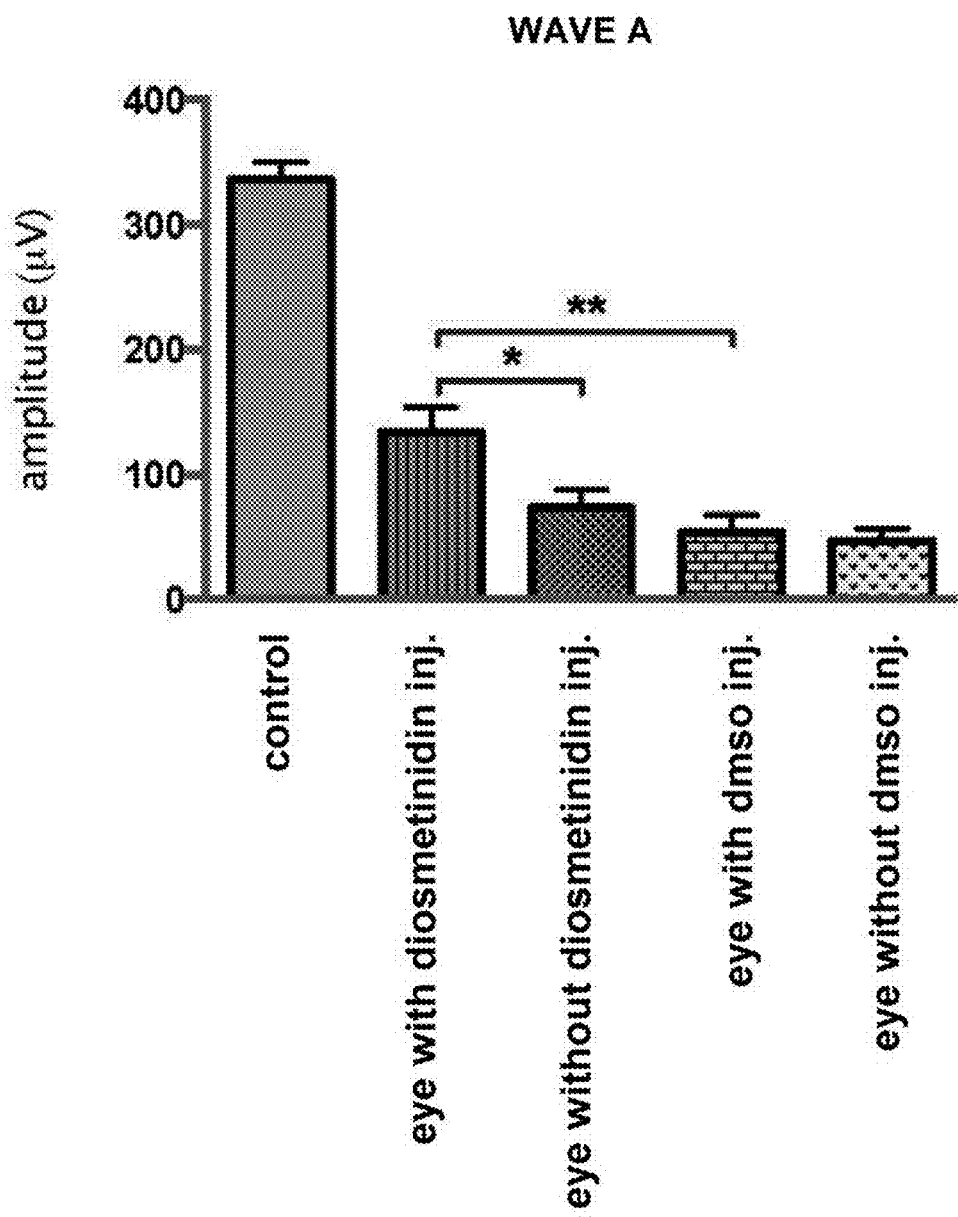
FIGS. 2 and 3 are graphs showing the electroretinograms of mice one week after the induction of the phototoxicity. The wave A (FIG. 2) shows the electrical activity of the photoreceptors, and the wave B (FIG. 3) shows that of the cells of the inner retina. The data were analysed statistically by an analysis of the variance followed by a Dunnett test. *$p<0.05$, $p<0.01$, *$p<0.001$.
Figure 3:
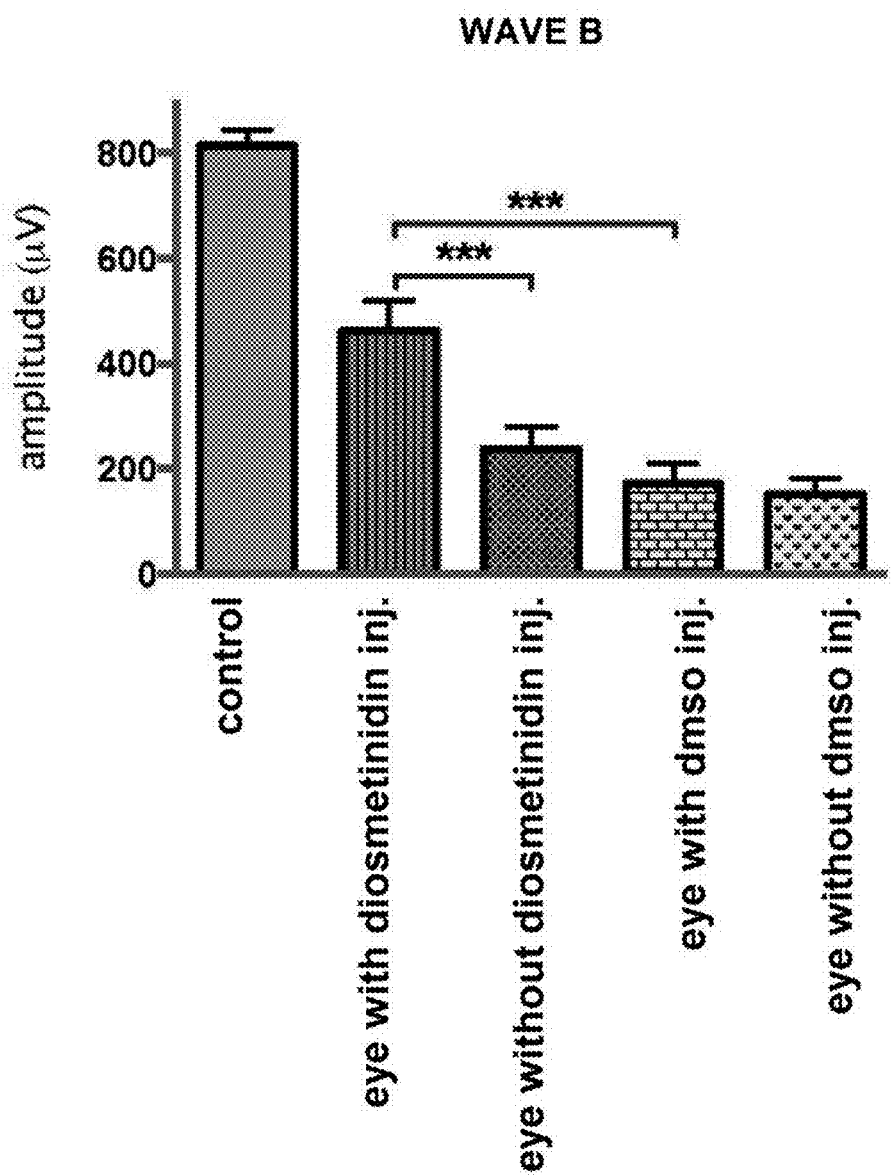
Figure 4:
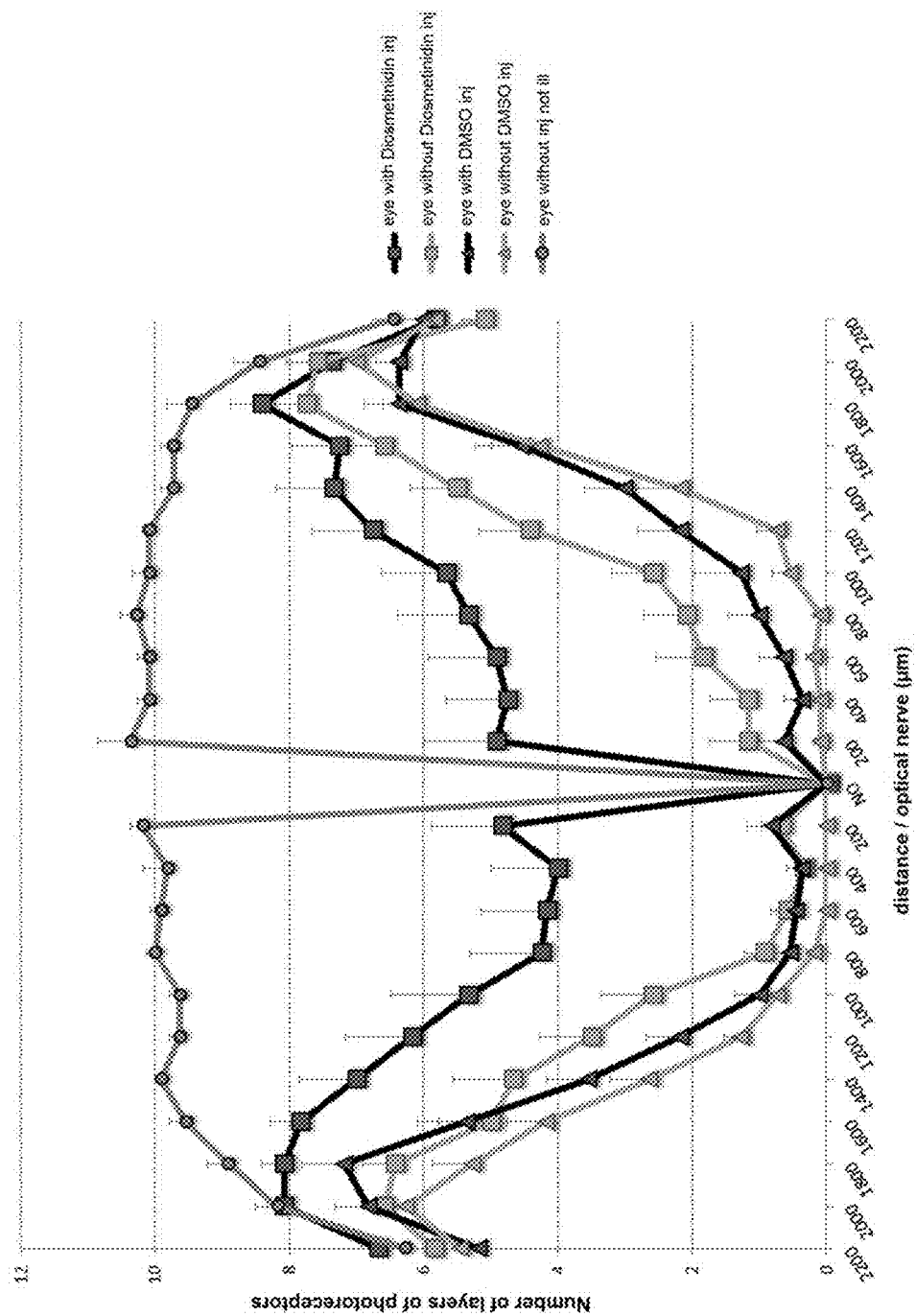
FIG. 4 is a graph showing the number of layers of photoreceptors according to the distance from the optical nerve after intravitreous injection of diosmetinidin.

The electroretinograms carried out 7 days later showed a protective effect of the diosmetinidin, of which the presence made it possible to maintain significant electrical activity (FIGS. 2 and 3) and good survival of the photoreceptors (FIG. 4).

The invention claimed is:

1. A method for treating and/or stabilising AMD, Stargardt disease, pigmentary retinopathy and/or diabetic retinopathy, comprising the administration to a patient in need thereof of an effective amount of a compound of Formula I

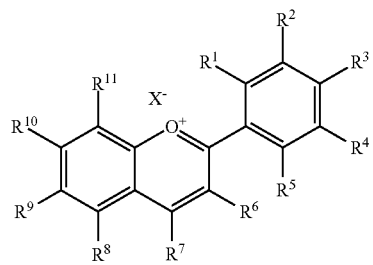

wherein
$R^1$, $R^2$, $R^3$, $R^4$ and $R^5$ each independently is a group selected from hydrogen, halo, hydroxyl, alkoxy, aryloxy, heteroaryloxy, acyloxy, alkyl, aryl, aralkyl, alkylaryl, alkenyl, nitro, nitrile, amino, with the condition that at least one of $R^1$, $R^2$, $R^3$, $R^4$ or $R^5$ is a hydroxyl;
$R^6$ is hydrogen;
$R^7$ is a group selected from hydrogen, halo, hydroxyl, alkoxy, aryloxy, heteroaryloxy, acyloxy, alkyl, aryl, aralkyl, alkylaryl, alkenyl, nitro, nitrile, amino;
$R^8$, $R^9$, $R^{10}$ and $R^{11}$ each independently is a group selected from hydrogen, halo, hydroxyl, alkoxy, aryloxy, heteroaryloxy, acyloxy, alkyl, aryl, aralkyl, alkylaryl, alkenyl, nitro, nitrile, amino, with the condition that at least one of $R^8$, $R^9$, $R^{10}$ or $R^{11}$ is a hydroxyl; and
$X^-$ is an anion selected from: anion derived from a mineral acid; anion derived from an organic acid; or an anion derived from a sulphate or sulphonate group.

2. The method according to claim 1, wherein the anion derived from a mineral acid is selected from a bromide, chloride, borotetrafluoride and perchloride anion; and wherein the anion derived from an organic acid is selected from an acetate, borate, citrate, tartrate, bisulphate, sulphate and phosphate anion.

3. The method according to claim 1, wherein the compound is of Formula Ia

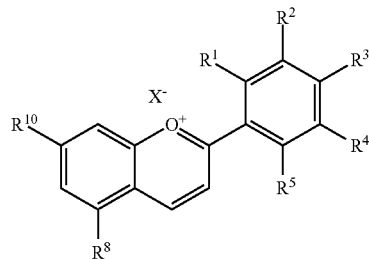

wherein $R^1$, $R^2$, $R^3$, $R^4$, $R^5$, $R^8$, $R^{10}$ and $X^-$ are such as defined in claim 1.

4. The method according to claim 1, wherein:
$R^1$, $R^2$, $R^3$, $R^4$ and $R^5$ each independently is a group selected from hydrogen, hydroxyl and alkoxy, with the condition that at least one of $R^1$, $R^2$, $R^3$, $R^4$ or $R^5$ is a hydroxyl; and
$R^8$ and $R^{10}$ each independently is a group selected from hydrogen, hydroxyl and alkoxy, with the condition that at least one of $R^8$ or $R^{10}$ is a hydroxyl.

5. The method according to claim 1, wherein the compound is of Formula Ib

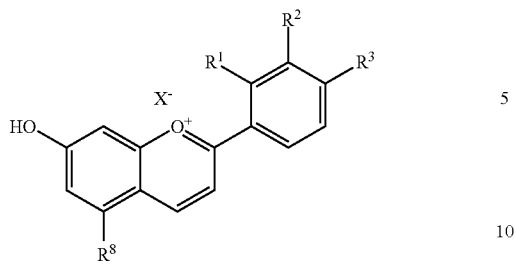

wherein $R^1$, $R^2$, $R^3$, $R^8$ and $X^-$ are such as defined in claim 1.

6. The method according to claim 1, wherein $R^8$ is a hydrogen atom.

7. The method according to claim 1, wherein the compound is selected from:
- 2',7-dihydroxy-4'-methoxy-flavylium chloride;
- 2',3',7-trihydroxy-4'-methoxy-flavylium chloride;
- 3',7-dihydroxy-4'-methoxy-flavylium chloride;
- 4',5,7-trihydroxy-flavylium chloride;
- 3',5,7-trihydroxy-4'-methoxy-flavylium chloride;
- 3',4',5',5,7-pentadroxy-flavylium chloride; and
- 3',4',5,7-tetrahydroxy-flavylium chloride.

* * * * *